United States Patent [19]

Mull

[11] 4,148,304
[45] Apr. 10, 1979

[54] DEVICE FOR MEASURING OVULATION

[75] Inventor: Leland G. Mull, Vienna, Va.

[73] Assignee: BMD Development Trust, Washington, D.C.

[21] Appl. No.: 745,989

[22] Filed: Nov. 29, 1976

[51] Int. Cl.$^2$ ............................................. A61B 5/05
[52] U.S. Cl. .................................. 128/2 R; 128/2 H; 128/2.1 R
[58] Field of Search ............... 128/2 R, 2 H, 2.1 R, 128/2.05 C, 2.1 C, 2.1 E

[56] References Cited

U.S. PATENT DOCUMENTS

| | | | |
|---|---|---|---|
| 2,247,875 | 7/1941 | Ellis | 128/2.1 R |
| 3,054,397 | 9/1962 | Benzinger | 128/2 H |
| 3,207,151 | 9/1965 | Takagi | 128/2.1 C |
| 3,844,276 | 10/1974 | McDougall | 128/2.1 E |
| 3,910,257 | 10/1975 | Fletcher et al. | 128/2 H |
| 3,924,609 | 12/1975 | Friedenberg et al. | 128/2.1 R |
| 4,023,094 | 5/1977 | Adams | 128/2 H |
| 4,031,365 | 6/1977 | Raggiotti et al. | 128/2 H |

OTHER PUBLICATIONS

Dickey, Wm. T. et al., "Body Temperature Monitoring via the Tympanic Membrane", Surgery, v. 67 #6, Jun. 1970, pp. 981–984.

Primary Examiner—Robert W. Michell
Assistant Examiner—Francis J. Jaworski
Attorney, Agent, or Firm—George R. Douglas, Jr.; Anthony D. Cennamo; Sherman Levy

[57] ABSTRACT

A system for determining the time of ovulation in females including a probe which measures the body temperature and a probe which measures body potential of a female subject, an electronic amplification circuit and an indicating device which is capable of measuring small changes in temperature and body potential of the subject thereby providing a portable and convenient device for determining time of ovulation.

2 Claims, 6 Drawing Figures

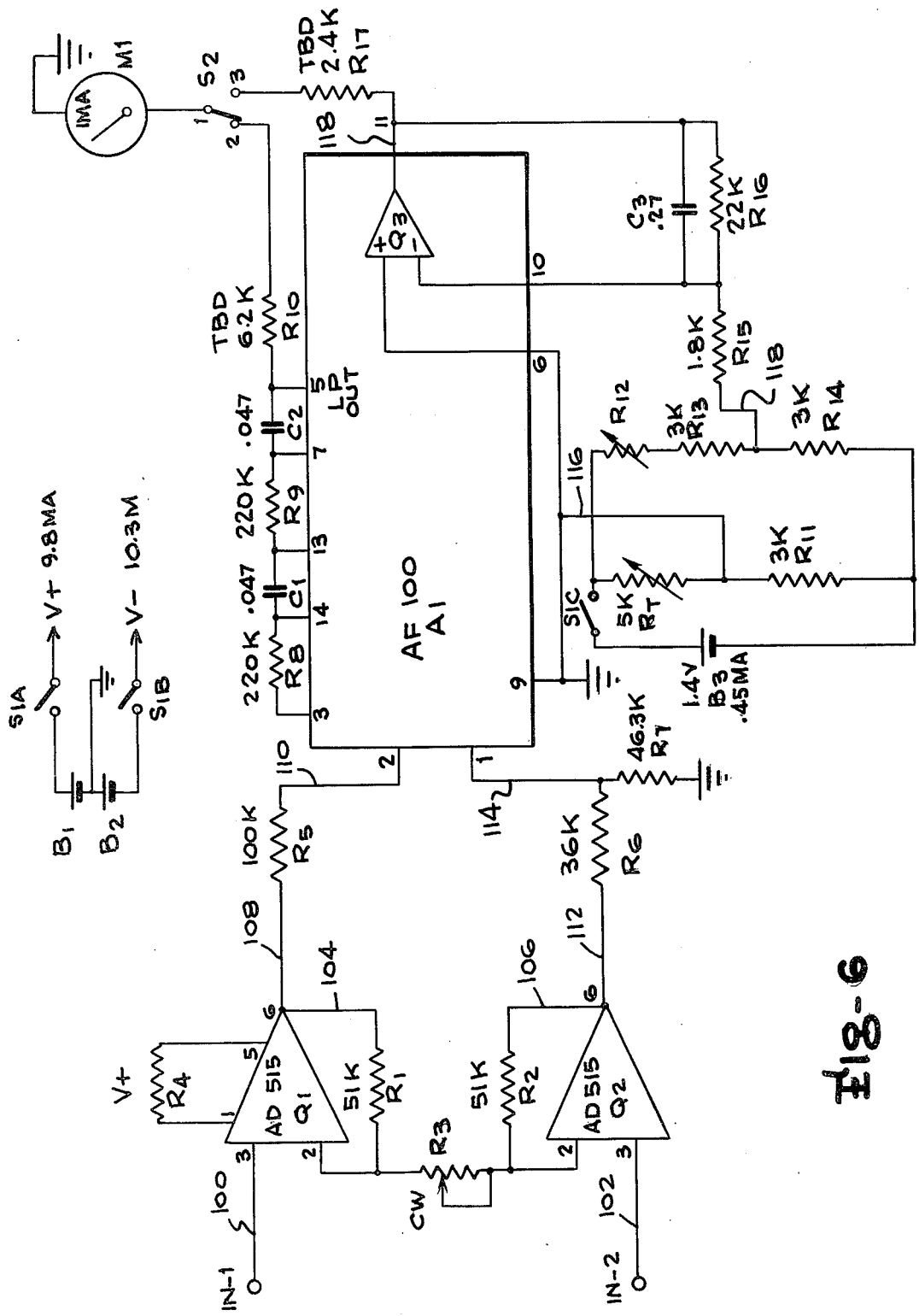

DEVICE FOR MEASURING OVULATION

BACKGROUND OF THE INVENTION

This invention relates to devices for assisting in birth control and more particularly relates to a device for determining the time of ovulation by indicating temperature and body potential changes in the female subject through use of easily applied temperature and body potential probes, electronic circuitry and an indicating device.

Over the years, countless number of women, who have for various reasons abstained from the use of clinical and mechanical contraception, have found to their great dismay that natural fertility control practices such as the rhythm or cyclical methods for avoiding pregnancy, are inefficient and quite unreliable. The reason for this inefficiency and unreliability is caused by their being no fixed relationship between ovulation and menstruation, for either may exist without the other. Consequently, women practicing natural fertility control cannot be certain of avoiding an unwanted pregnancy through the abstention of intercourse, unless they known exactly when they are ovulating. The same inefficiency and unreliability exists for one who tries to conceive, but fails time and time again because the time of ovulation is poorly defined and therefore cannot be optimized. An urgent demand for this type of instrumentation has long been realized by those who known that the female productive cycle varies from woman to woman and that the only way for an individual to avoid pregnancy is to know her own particular time of ovulation.

Previously, oral or anal temperatures have been measured, however, these temperatures have not been sufficiently reliable. Voltage gradients have also been measured, however, the equipment has been very large and expensive.

It has been stated that "The development of a simple method of detecting accurately the time of ovulation in women, especially in advance, would warrant almost unlimited research effort."The basis for this statement being that in addition to the harmful side effects of most chemical or mechanical contraceptives, the practice based on rhythm methods or basal body temperatures have been found ineffective as a contraceptive method is no less than 30% of all women. All over the world, individuals, organizations and authorities are acutely concerned with the exploding population.

Therefore, it is the primary object of this invention to provide a new and improved device for determining the time of ovulation in a subject female.

Another object of the present invention is to provide a device which is efficiently designed and easily operated to make it feasible for any woman to determine the time of her ovulation.

A further object of the present invention is to provide a device for determining the time of ovulation which may be utilized for either contraceptive or fertility aid according to the needs of the subject female.

A still further object of the present invention is to provide a device which assists in contraception without producing the harmful side effects of most chemical or mechanical contraceptives.

Another object of the present invention is to provide a device which will assist in determining the exact time of ovulation thereby improving the reliability of the rhythm method of contraception.

An additional object of the present invention is to provide a device for determining the time of ovulation which is relatively simple and foolproof yet can be mass produced and sold at economical prices so as to put the device in the reach of most women for home use.

A further object of the present invention is to provide a device for determining the time of ovulation to assist in determining the period of fertility for females who desire to become pregnant.

An additional object of the present invention is to provide a device for the determination of the time of ovulation including electronic circuitry to condition the signals and provide a readout device having the capability of indicating small changes in temperature and voltage gradient and a long term stability for home use.

Another object of the present invention is to provide a device for determining the time of ovulation which is small, portable and convenient for home use.

Other objects and advantages of the present invention will become more apparent to those persons skilled in the art to which the present invention relates from the following description taken in conjunction with the accompanying drawings, wherein:

FIG. 6 is a schematic diagram of the circuitry according to the present invention.

Figure 1:
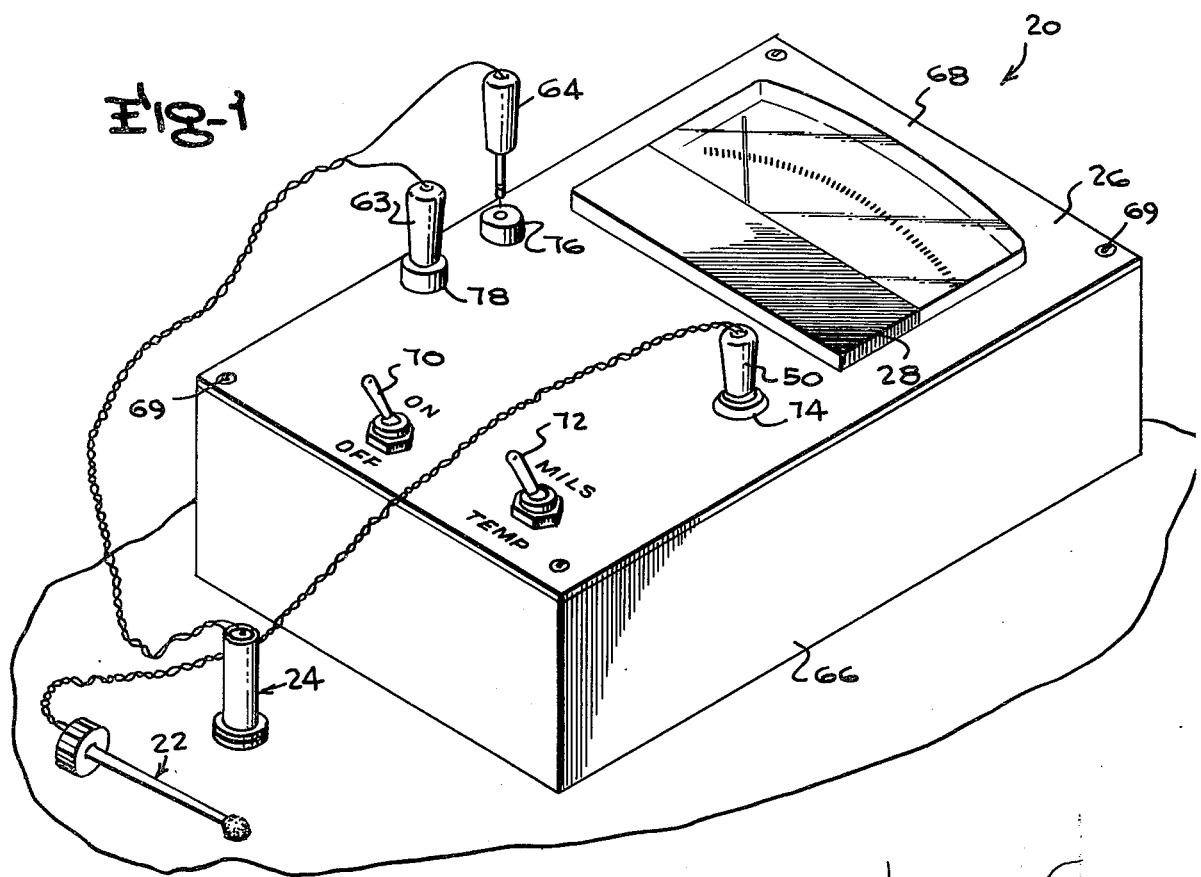
FIG. 1 is a perspective view of a preferred embodiment of the present invention showing the indicating meter and the temperature probe and the voltage gradient probe.

Attention is initially invited to FIGS. 1 through 6 of the drawings which illustrate the various components of the prederred embodiment 20 of the invention including a temperature probe 22, a voltage gradient probe 24 and an indicating package 26 with an indicating meter 28.

Figure 2:
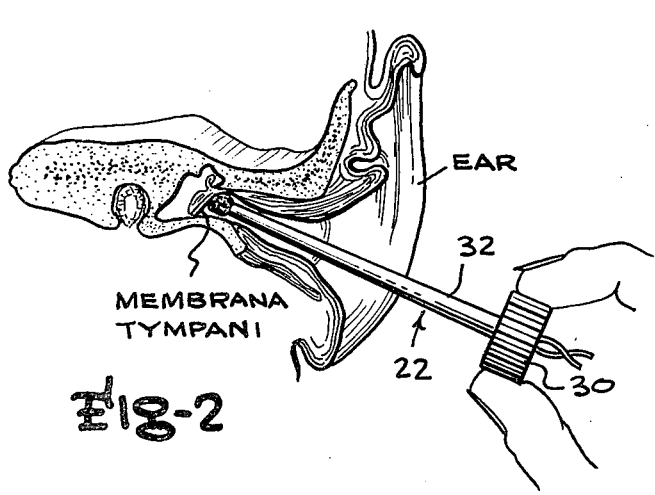
FIG. 2 is a fragmentary cross-sectional view of the ear of the subject female with the temperature probe inserted to measure the temperature at the tympanic membrane.
Figure 3:
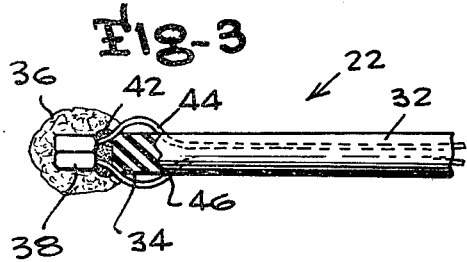
FIG. 3 is a fragmentary cross sectional view of the thermistor portion of the temperature probe shown in FIG. 2.

As indicated in FIG. 2 and FIG. 3, the temperature probe 22 includes a finger grip shoulder 30, a probe support 32 which is fixed at one end to the finger portion 30 and carries the sensor portion 34 at the opposite end. A thermistor 38 of conventional configuration produces a voltage output which is proportional to the temperature of the tympanic membrane and may be covered with cotton 36 or the like to prevent injury to the ear of the user. The thermistor 38 being retained in the probe head 34 by an adhesive material 42. Lead wires 44 and 45 from the thermistor 38 pass through the probe support 32, as indicated in FIGS. 2 and 3 and pass through holes in the finger portion 30 as suggested in FIG. 1. The lead wires are then twisted together with their opposite ends being connected to a jack 48 of the type used in radio equipment.

Figure 4:
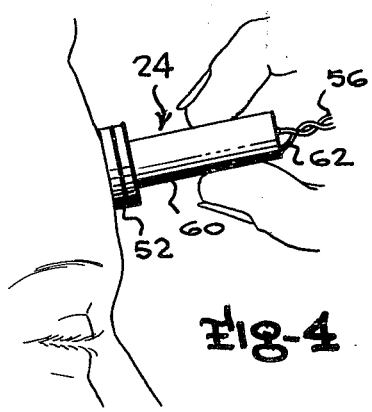
FIG. 4 illustrates the voltage gradient probe applied to the forehead of the subject female.
Figure 5:
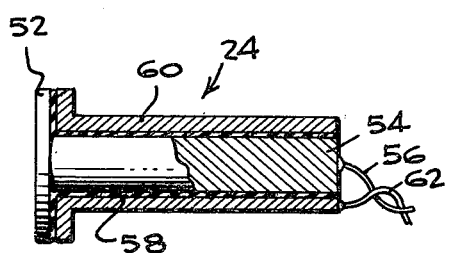
FIG. 5 is a partial cross sectional view of the voltage gradient probe shown in FIG. 4.

As best indicated in FIGS. 4 and 5, voltage gradient is measured on the body of the subject female by the voltage gradient probe 24 which includes a contact disc 52 formed of a conductive material such as brass or silver and having a rearwardly extending cylindrical post 54 integrally formed with the contact disc 52. A lead wire 56 is attached to the free end of the post 54 by soldering or the like. An insulating collar 58, formed of Mylar or other material with good insulating characteristics, covers the rear surface of the contact disc 52 and the outer surface of the cylindrical post 54 to insulate the contact disc 52 from an outer contact cylinder 60 which is concentric with the cylindrical post 54 and the insulating collar 58. The outer contact cylinder 60 provides a contact surface for the finger tips of the user as shown in FIG. 4. The second lead wire 62 from the voltage gradient probe is attached to the outer contact 60 by soldering or the like, as shown in FIG. 5, and is twisted with the first lead wire 56, as shown in FIG. 1, with the opposite ends of the lead wires attached to the jack post 63 and to a voltage gradient input jack 64.

The housing for the indicating package 26 is of conventional construction having a lower box portion 66 and a cover plate 68 attached to the box portion 66 by mounting screws 69 located at the corners of the cover plate 68 and threadingly engaging the box portion 66 to retain the cover plate in position.

Mounted on the cover plate 68 is the indicating meter 28 which is a conventional milliampmeter meter, an on-off switch 70 for activating the device, an indicating switch 72 which permits measurement of temperature or voltage gradient depending on the desired reading, a temperature input socket 74 for receiving the temperature input jack 50, a voltage gradient input socket 76 for receiving the voltage gradient input jack 64 and a ground socket 78 for receiving the jack 63.

Operation of the device according to the present invention is accomplished with two modes of operation for the determination of the time of ovulation. Although a single meter is used to indicate the desired reading, both the temperature measurement and the voltage gradient measurement are taken independently of the other and therefore read out separately although the two measurements could be taken simultaneously and be read out as a single indication of the state of ovulation. These two measurements, however in the embodiment shown, are normally taken one right after the other by merely switching the selecting switch 72 and holding the probes against the foregoing or against the tympanic membrane as indicated in FIGS. 2 and 4. The indicating meter 28 has a scale which is used for either temperature or voltage gradient readings. Digital readout devices could be used in place of the indicating meter. Since every woman may vary somewhat on her "base-line" reading, which is established by taking daily measurements for a period of at least thirty days to isolate the duration of ovulation, it is important to establish this "base-line" reading through daily readings taken at least once a day.

Preferred times are upon awakening in the morning and before any activity. Generally, thirty to sixty consecutive daily readings will be sufficient to determine the normal base-line and once this is established, a color coding can be placed on the face of the indicator meter 28 to represent stages of the menstrual cycle as determined by the temperature and voltage gradient measurements.

The device according to the present invention will detect a change in temperature and voltage gradient of the magnitude representing ovulation. This condition will be clearly evident from the meter reading once the normal level is known; however, the extent and duration of the magnitude of the change will vary among women according to their age, state of health, use of hormonal medication, etc.

The actual measurement of the temperature and voltage levels is a two-step process according to the present invention. First, the subject should insure that the input jacks 50, 63 and 64 are securely inserted into the sockets 74, 76 and 78, as indicated in FIG. 1. The on-off switch 70 should then be moved to the "on" position. The device is now ready for use to measure either the temperature or voltage gradient of the user. The measurement should be taken one immediately after the other. When completed in this manner, the two readings serve to compliment each other and insure the greater likelihood of accurately determining the onset of ovulation.

For measurement of temperature, the indicator switch 72 is moved to the "Temp" position as indicated in FIG. 1. The finger grip portion 30 of the temperature probe 22 is grasped between the fingers and the probe is gently positioned in the ear adjacent the tympanic membrane as indicated in FIG. 2. The indicator member 28 is then read and the number indicated is recorded.

For measurement of the voltage gradient, the indicator switch 72 is positioned in the "Mils" position representing a milivolts reading for the voltage gradient. The contact disc 52 is positioned as shown in FIG. 4, against the forehead by grasping the contact cylinder 60 between the thumb and index finger. The indicator meter 28 is read and the number indicated is recorded. After the measurements have been completed, the on-off switch 70 may be returned to the "off" position as indicated in FIG. 1. Since actual measurement requires only a few seconds, a relatively long life of the battery is anticipated if the device is activated only during the periods when measurements are being taken. Evidence that the battery is weak, may be indicated when the meter fails to reach the normal reading level. A battery condition switch may also be added to the front panel.

The circuitry for the invention as shown in FIG. 6 will now be discussed. Very high input operational amplifiers $Q_1$ and $Q_2$ having high input impedances in the range of $10^{14}$ ohms are connected as a differential type amplifier to provide a high common mode noise rejection. Input from the voltage gradient probe 24 is provided through IN-1 from the input jack 64 and to terminal IN-2 from the jack 63 as shown in FIGS. 1 and 6. Input from the temperature gradient probe 22 is provided by the thermistor 38 identified as $R_T$ in the schematic of FIG. 6 to be discussed hereafter. Input to amplifier $Q_1$ is received from terminal IN-1 through input lead 100 and amplifier $Q_2$ receives inout through input lead 102. The gain of the amplifiers $Q_1$ and $Q_2$ is controlled by feed back resistors $R_1$ and $R_2$ through output leads 104 and 106 with potentiometer $R_3$ providing gain calibration for the amplifiers. Resistors $R_4$ and $R_5$ provide impedance matching and in conjunction with resistors $R_6$ and $R_7$ establish the Q of a tuned filter section $A_1$. Resistor $R_5$ receives the output of amplifier $Q_1$ through lead 108 and provides input through lead 110 to the tuned filter section $A_1$. The output from amplifier $Q_2$ flows through output lead 112 to resistor $R_6$ and into the tuned filter section $A_1$ through input lead 114. Resistors $R_8$ and $R_9$ and capacitors $C_1$ and $C_2$ permit tuning of the filter section $A_1$ which tuning is accomplished by the pre-selected values of the components; in the practice of the present art of filters, it is contemplated within the scope of the art that one may be provided with continuously variable, tweakable elements capable of adjustment during use of the system. This in itself may not be invention and is not presently shown. The correct current to the indicating meter $M_1$, shown as indicating meter 28 in FIG. 1, is established by resistor $R_{10}$ when switch $S_2$ provides contacts through terminals 1 and 2 of the switch as shown in FIG. 6 with the switch $S_2$ being indicator switch 72 thereby permitting the selection of voltage or temperature indication.

A temperature sensitive bridge is formed by the thermistor 38 identified as $R_T$, resistor $R_{11}$, potentiometer $R_{12}$, resistor $R_{13}$, $R_{14}$ and a battery $B_3$ as shown in FIG. 6. Potentiometer $R_{12}$ permits calibration of the temperature indication on the indicating meter $M_1$. The bridge difference voltage across outputs 116 and 118 is amplified from amplifier $Q_3$ which is sufficient to drive the indicating meter $M_1$. The amplifier gain being established by resistors $R_{15}$ and $R_{16}$ while capacitor $C_3$ is used to limit response to any stray alternating voltage. Current is limited to the indicating meter $M_1$ by resistor $R_{17}$ connected between the output 118 from the amplifier $Q_3$ and terminal 3 on switch $S_2$. Power is supplied to the units by batteries $B_1$ and $B_2$ when the on-off switch $S_1$ is activated which occurs when switch 70, shown in FIG. 1, is moved. Additionally, battery $B_3$ provides power to the temperature sensitive bridge when power switch $S_1$ is activated.

The circuit, as described, provides a device according to the present invention with characteristics important to the success of the device. First, it provides a very high impedance differential amplifier to minimize the effect of differing skin resistance. Additionally, it provides a low pass filter with pass band cutoff of not more than 4.5 hertz to reject any response from ambiient electrical noise or outflow of data waves from the subject. Further, it provides a temperature measuring circuit that is stable over a long period of time with approximately 4° C. meter scale for ease of viewing small changes in body temperature. Low quiescent supply voltage is provided for long battery life and integrated circuitry provides reliability, small size and minimum weight.

Numerous modifications of the subject invention will undoubtedly occur to those skilled in the art; therefore, it should be understood that the spirit and scope of the invention is to be limited solely in light of the appended claims.

I claim:

1. A device for deriving improved data for determining the time of ovulation of a female subject, said device comprising in combination means for measuring a predetermined voltage potential and adaptable for placement between two spaced apart locations on the body of the subject, means for measuring a pedetermined temperature of the subject and adaptable for placement at a predetermined location on the body of the subject, means for indicating said voltage potential and said temperature thereby permitting determination of the time of ovulation of the subject, said predetermined location for measuring the predetermined temperature of the subject is the tympanic membrane in an ear of the subject, said spaced apart locations on the body for measurement of said predetermined voltage potential are the forehead and fingertip of said subject, said means for measuring said predetermined voltage potential includes electrodes placed in contact with the body of the subject at said predetermined locations, said means for measuring said predetermined temperature includes a thermistor placed in contact with the body of the patient, and said indicating means includes electronic means comprising a pair of high input resistance amplifiers having inputs connected to said electrodes, a tuned filter network receiving an input from an output of said resistance amplifiers, meter means for receiving an input from the output of said filter network to visually display an output which indicates the voltage potential on said electrodes, a temperature sensitive bridge having four legs with resistors in three legs thereof and said thermistor as the forth leg thereof, and a voltage potential across two legs thereof with an output from said temperature supplied from across two alternate legs thereof, an amplifier to receive the output from said temperature sensitive bridge and supply an input to said meter means for visually displaying an output which indicates the temperature of said thermister.

2. An improved method for determining the time of ovulation in a female subject, said method comprising in combination the steps of measuring a predetermined voltage potential between two spaced apart locations on the body of the subject, measuring a predetermined temperature of the subject at a predetermined location on the body of the subject, indicating said voltage potential and said temperature thereby permitting determination of the time of ovulation of the subject, said predetermined location for measuring the predetermined temperature of the subject is the tympanic membrane in an ear of the subject, said spaced apart locations on the body for measurement of said predetermined voltage potential are the forehead and a fingertip of said subject and wherein said step for measuring said predetermined voltage potential includes placement of electrodes in contact with the body of the subject at said predetermined locations, wherein said step for measuring said predetermined temperature includes placement of a thermistor in contact with the body of the patient, and wherein said indicating step includes processing data by electronic means comprising a pair of high input resistance amplifiers having inputs connected to said electrodes, a tuned filter network receiving an input from an output of said resistance amplifiers, meter means for receiving an input from the output of said filter network to visually display an output which indicates the voltage potential on said electrodes, a temperature sensitive bridge having four legs with resistors in three legs thereof and said thermistor has the fourth leg thereof, and a voltage potential across two legs thereof with an output from said temperature supplied from across two alternate legs thereof, an amplifier to receive the output from said temperature sensitive bridge and supply an input to said meter means for visually displaying an output which indicates the temperature of said thermister.

* * * * *